United States Patent [19]
Danner et al.

[11] Patent Number: 5,855,922
[45] Date of Patent: Jan. 5, 1999

[54] ANTISEPTIC COMPOSITION AND PROCESS FOR PROPHYLAXIS AND THERAPEUTIC TREATMENT OF DERMAL DISORDERS

[75] Inventors: Bobby C. Danner, Norman, Okla.; Hampar L. Karageozian, San Juan Catistrano, Calif.; James P. Ringo, Norman, Okla.

[73] Assignee: Bio-Cide International, Inc., Norman, Okla.

[21] Appl. No.: 568,745

[22] Filed: Dec. 7, 1995

[51] Int. Cl.⁶ .................................................. A61K 33/20
[52] U.S. Cl. ........................ 424/665; 424/661; 514/858; 514/859; 514/860; 514/861; 514/862; 514/863; 514/864; 514/865; 514/928
[58] Field of Search ..................... 424/661, 662, 424/665; 514/858, 859, 860, 861, 862, 863, 864, 865, 928

[56] References Cited

U.S. PATENT DOCUMENTS

| | | | |
|---|---|---|---|
| Re. 31,779 | 12/1984 | Alliger | 252/187.23 |
| 2,701,781 | 2/1955 | de Guevara | 167/17 |
| 3,271,242 | 9/1966 | McNicholas | 167/17 |
| 4,084,747 | 4/1978 | Alliger | 239/4 |
| 4,317,814 | 3/1982 | Laso | 424/130 |
| 4,330,531 | 5/1982 | Alliger | 424/149 |
| 4,507,285 | 3/1985 | Kuhne | 424/615 |
| 4,574,084 | 3/1986 | Berger | 424/128 |
| 4,689,215 | 8/1987 | Ratcliff | 424/53 |
| 4,696,811 | 9/1987 | Ratcliff | 424/53 |
| 4,725,437 | 2/1988 | Kuhne | 424/613 |
| 4,786,492 | 11/1988 | Ratcliff | 424/53 |
| 4,788,053 | 11/1988 | Ratcliff | 424/53 |
| 4,792,442 | 12/1988 | Ratcliff | 424/53 |
| 4,793,989 | 12/1988 | Ratcliff | 424/53 |
| 4,808,389 | 2/1989 | Ratcliffe | 424/53 |
| 4,818,519 | 4/1989 | Ratcliff | 424/53 |
| 4,837,009 | 6/1989 | Ractliff | 424/53 |
| 4,851,213 | 7/1989 | Ratcliff | 424/53 |
| 4,855,135 | 8/1989 | Ratcliff | 424/127 |
| 4,880,638 | 11/1989 | Gordon | 424/662 |
| 4,891,216 | 1/1990 | Kross et al. | 424/78 |
| 4,956,184 | 9/1990 | Kross | 424/661 |
| 4,986,990 | 1/1991 | Davidson et al. | 424/665 |
| 4,990,334 | 2/1991 | Longino et al. | 424/401 |
| 5,019,402 | 5/1991 | Kross et al. | 424/665 |
| 5,100,652 | 3/1992 | Kross et al. | 424/53 |
| 5,192,459 | 3/1993 | Tell et al. | 424/665 |
| 5,384,134 | 1/1995 | Kross et al. | 424/661 |
| 5,419,818 | 5/1995 | Wanngard | 204/95 |
| 5,623,725 | 4/1997 | Kross | 424/665 |

FOREIGN PATENT DOCUMENTS

| | | |
|---|---|---|
| 01265005 | 10/1989 | Japan . |
| WO 85/04107 | 9/1985 | WIPO . |

OTHER PUBLICATIONS

Chemical Abstracts 115:129522, 1991.
Medline Abstract, accession No. 89190173, 1989.
Chemical Abstracts 102:137809, 1985.

*Primary Examiner*—John Pak
*Attorney, Agent, or Firm*—Crow & Dunlevy

[57] ABSTRACT

Compositions and processes for the prophylaxis and therapeutic treatment of wounds, chronic non-healing wounds, burns, disease and other dermal disorders are disclosed. The compositions of the present invention comprise aqueous solutions of a metal chlorite having a concentration of from about 0.002% to about 0.5% by weight of metal chlorite. The process of the present invention comprises treating the dermal disorder with an aqueous solution of from about 0.002% to about 0.5% by weight of a metal chlorite. Wounds, chronic non-healing wounds, burns and other dermal disorders treated in this manner heal more quickly and with reduced scar formation. The antiseptic compositions and processes of the present invention exhibit anticollagenous activity such that the characteristics of the healed skin, such as elasticity and tensile strength, are similar to undamaged skin.

8 Claims, No Drawings

ANTISEPTIC COMPOSITION AND PROCESS FOR PROPHYLAXIS AND THERAPEUTIC TREATMENT OF DERMAL DISORDERS

BACKGROUND OF THE INVENTION

1. Field of the Invention

The present invention involves the treatment of dermal disorders, wounds and infections in humans and is more particularly directed toward compositions and methods for the treatment and prophylaxis of dermal wounds, chronic non-healing wounds, burns, disease, and other dermal disorders.

2. Discussion

As human skin lost its hair cover through the centuries, it underwent many adaptive changes which gave it strength and resilience. The outer layer, while remaining thin to allow suppleness, attained remarkable biological ruggedness, protecting the skin from physical and chemical injury and from the invasion of micro-organisms. Human skin is elastic to accommodate size increases and decreases of the body it encases and to accommodate the many subtle movements that characterize the human body.

Continuously exposed to trauma, human skin has inherent mechanisms that enable it to adapt to new situations and to withstand the onslaught of injurious environmental conditions. Skin repairs expertly and with dispatch the perennial minor injuries it suffers and, given an opportunity, repairs major injuries as well. Many injuries to the skin, such as burns or cuts, however, result in healed skin that displays scarring as well as reduced elasticity, tensile strength and other characteristics. The scarred skin is not only less aesthetically appealing, but also less functional.

The surface of the skin is normally never sterile. At birth, or soon after, it becomes populated with germs, which all but the most stringent measures fail to remove. These pathogenic microorganisms are ubiquitous and, as opportunistic parasites, usually become invasive and infectious when the body's normal barriers to infection are compromised. Examples of the compromise of dermal barriers include disruption of the physical integrity of the skin by puncture or other trauma, burns, pressure wounds from bedridden patients, and immune compromised patients, e.g., patients undergoing chemotherapy or radiation therapy. Numerous microbial infections are associated with skin disease and, for illustrative purposes only, a few of these types are presented as follows.

One of the many types of bacterial skin disease is impetigo, a localized infection of the skin superficial layers, which is caused by an infection of Streptococcus bacteria usually in association with Staphylococcus. Dermal fungal mycoses are caused by three genera of closely related fungal dermatophytes which infect superficial keratinized tissues particularly the skin, hair, and nails. These mycelial fungi can infect the skin and cause common diseases such as *Tinea pedis* (Athletes foot), *Tinea corporis* (Ringworm), and *Tinea capitis* (Ringworm of the scalp).

Viruses which are causative agents of localized infections of the skin and mucous membranes are well known. Herpes simplex virus can cause vesicular eruptions of the skin or mucous membranes and papilloma viruses can cause benign skin tumors commonly know as warts. Anaerobic and aerobic bacteria may act independently or synergistically to form infections of the skin and soft tissues usually as a result of trauma or wounds. Gangrene and cellulitis are examples of this type of skin and soft tissue disease resulting from bacterial infection. Additionally, nosocomial infections by antibiotic resistant Staphylococci present a major problem for infection control in modern hospitals, particularly to patients requiring invasive treatments such as surgery.

Certainly it is in man's best interest to heal dermal disorders as quickly as possible, and for the healed skin to have the same characteristics as undamaged skin. In this manner the body's primary barrier to infection is restored, and the healed skin is both aesthetically appealing and functions as well as undamaged skin. Unfortunately, though, man is still hopelessly ignorant about many of the anatomical, physiological, and biochemical properties of skin and about most of its numerous disorders. To date, much of man's effort to facilitate the healing of dermal disorders has focused on prevention of microbial infection. Innumerable compounds have been tested in an attempt to discover an effective antiseptic for treating and preventing microbial infection. Antiseptics are substances that check the growth or action of microorganisms, especially in or on living tissue. At one time, tincture of iodine was among the most widely used antiseptics, but suffered the well-known drawback of being very irritating to the body tissues. Various chlorine compounds have since been found to have strong antiseptic properties with much lower irritating characteristics. Chlorine dioxide ($ClO_2$) and "stabilized" chlorine dioxide have been found to be especially desirable antiseptics.

Chlorine dioxide is an oxidizing agent which has strong biochemical activity. In industrial applications, chlorine dioxide is generally regarded as superior even to gaseous chlorine in eliminating algae and other organic material in addition to removing odors and tastes. Chlorine dioxide is also considered as effective as chlorine gas, if not more effective, as a bactericide, virucide and sporicide. Biochemically, however, chlorine dioxide functions in many ways other than as a mere germicide, as noted in U.S. Pat. No. 4,855,135. These other functions include: (a) oxidation of double bonds between two carbon atoms; (b) oxidation of unsaturated fatty acids (lipids) via double bonds between two carbon atoms; (c) acceleration of hydrolysis of carboxylic anhydrides; (d) oxidation of aldehydes to the corresponding carboxylic acids; (e) oxidation of alcohols; (f) oxidation of amines; (g) oxidation of phenols, phenolic derivatives and thiophenolic compounds; (h) moderate oxidation of hydroquinones; (i) oxidation of amino acids, proteins and polyamides; (j) oxidation of nitrates and sulphides; and (k) alteration of the CHO and $CH_2OH$ radicals of carbohydrates to produce carboxylic functions. Thus, chlorine dioxide is a highly reactive, unstable radical and its biochemical reaction is one of strong oxidation.

Concentrated chlorine dioxide in its liquid or gaseous state is highly explosive and poisonous. This danger prohibits the use of chlorine dioxide in a concentrated form by all but the largest and most sophisticated users. Smaller and somewhat less sophisticated users have often produced chlorine dioxide by acidification of chlorite, a chlorine dioxide liberating compound available in both powder and liquid form. Acid generation of chlorine dioxide has been reported in the literature using a wide variety of inorganic and organic acids. Generally, any acid may be used including strong acids such as hydrochloric acid and sulfuric acid and relatively weak acids such as citric and tartaric acid.

A drawback of acid-induced generation of chlorine dioxide, though, is that it does not result in a stable chlorine dioxide generating solution, but instead provides a rapid generation of chlorine dioxide. The result is a relatively short generation of chlorine dioxide, after which the solution has few, if any, disinfecting characteristics. Increasing the concentration of chlorite and acid prolongs the period of chlorine dioxide generation but can lead to toxicity problems as well as generation of more chlorine dioxide than is required.

There have been numerous attempts to control the rate of production of chlorine dioxide, and all have met with limited success. For instance, U.S. Pat. No. Re. 31,779 (a reissue of U.S. Pat. No. 4,084,747) to Alliger discloses a germ-killing composition comprising a water soluble chlorite, such as sodium chlorite, and lactic acid. As disclosed therein, the particular composition possesses improved disinfectant properties, properties not attained by using the same composition but replacing the lactic acid with other acids such as phosphoric acid, acetic acid, sorbic acid, fumaric acid, sulfamic acid, succinic acid, boric acid, tannic acid, and citric acid. The germ-killing composition is produced by contacting an acid material containing at least 15% by weight of lactic acid with sodium chlorite in aqueous media, the amount of lactic acid being sufficient to lower the pH of the aqueous media to less than about 7. The methods disclosed of disinfecting and sanitizing a germ-carrying substrate, such as skin, include either application of the germ-killing composition, or application of the reactants to provide in situ production thereof.

Other patents disclose acid induced generation of chlorine dioxide from a metal chlorite by defining the chlorite concentration in terms of a limiting chlorous acid concentration. For example, U.S. Pat. No. 5,384,134 to Kross et al. discloses a method for treating dermal disorders wherein a first gel, which comprises a metal chlorite, is mixed with a second gel, which comprises a protic acid. The chlorite ion concentration in the form of chlorous acid is limited to no more than about 15% by weight of the total amount of chlorite ion concentration in the composition. The mixture of the two gels purportedly generates chlorine dioxide over an extended time of up to 24 hours.

Others refer to "stabilized" chlorine dioxide as a means of chlorine dioxide generation. The term stabilized chlorine dioxide refers to various compositions in which the chlorine dioxide is believed to be held in solution in the form of a labile complex. The stabilization of chlorine dioxide by the use of perborates was disclosed in U.S. Pat. No. 2,701,781 to de Guevara. According to the de Guevara patent, an antiseptic solution of stabilized chlorine dioxide can be formed from an aqueous solution of chlorine dioxide and an inorganic boron compound with the boron compound and the chlorine dioxide being present in the solution as a labile complex. The chlorine dioxide, fixed in this stable condition, is an essential ingredient of the antiseptic solution. The de Guevara patent discloses that the chlorine dioxide may be introduced into the compositions either by generation in situ or by external generation and subsequent introduction, such as by bubbling into the aqueous solution. Various methods may be employed for the external production of the chlorine dioxide, such as reaction of sulfuric acid with potassium chlorate or the reaction of the chlorate with moist oxalic acid. Alternatively, chlorine dioxide can be generated in situ by reaction of potassium chlorate and sulfuric acid. Note that whether the chlorine dioxide is produced in situ or externally, it is essentially an acid induced liberation of the chlorine dioxide from potassium chlorate.

U.S. Pat. No. 3,271,242 issued to McNicholas et al. also describes methods for preparing aqueous solutions of stabilized chlorine dioxide for use as antiseptic or bleaching agents. The McNicholas et al. reference discloses generating chlorine dioxide in any well-known manner, such as by the method of Example II of the de Guevara patent, and bubbling it into a solution of water containing a peroxy compound. According to the McNicholas et al. reference, in such solutions the chlorine dioxide is said to be retained in the solution as a labile complex when the solution is alkaline, and is released when the solution becomes acid. For antiseptic use, the reference discloses that the pH of the solution preferably is neutral or slightly alkaline. The chlorine dioxide molecule is said to be released from solution when in a slightly acid environment, such as that associated with the presence of bacteria. It is important to note, however, that the peroxy compounds present in the solution are themselves strongly oxidizing and capable of serving as an antiseptic agent. It is also important to note the methods disclosed rely on acid induced generation of chlorine dioxide.

Much less research has been devoted to the development of compositions and processes for the treatment of dermal disorders which function to facilitate the rapid healing of the skin and to achieve healed skin with the same appearance and characteristics as undamaged skin. U.S. Pat. No. 4,317,814 issued to Laso describes stabilized chlorine dioxide preparations for treatment of burns in humans. Aqueous mixtures of perborate stabilized solutions of chlorine oxides, such as chlorine dioxide, in combination with glycerin are described for topical application to burned areas and may also be administered by oral application for treatment of burns. The aqueous solutions of perborate stabilized chlorine oxides are disclosed as being prepared by mixing with water the following: sodium chlorite, sodium hypochlorite, hydrochloric acid, sulfuric acid, an inorganic perborate, and a peroxy compound, such as sodium perborate. Thus, the solutions prepared in accordance with the Laso patent contain chlorine dioxide, hypochlorite and peroxy compounds as strong oxidizing agents and appear to utilize acid activation of the chlorine dioxide. The Laso patent states that the methods disclosed therein resulted in an immediate subsidence of burn related pain in many cases. The patent describes healing as rapid and characterized by an absence of infection and contraction. Burn scars were smooth and resembled normal tissue, thus eliminating the need for plastic surgery in certain cases.

Antibiotic compounds have also been commonly used for the therapeutic treatment of burns, wounds and skin infections. While antibiotics may provide an effective form of treatment, several dangers are often associated with the use of antibiotics in the clinical environment. These dangers may include but are not limited to: (1) changes in the normal flora of the body, with resulting "superinfection" due to overgrowth of antibiotic resistant organisms; (2) direct antibiotic toxicity, particularly with prolonged use which can result in damage to kidneys, liver and neural tissue depending upon the type of antibiotic; (3) development of antibiotic resistant microbial populations which defy further treatment by antibiotics.

While the above efforts have met with some success, there continues to be a need for new compositions useful in facilitating the healing of dermal disorders which would preferably include antiseptic properties and low levels of irritation and toxicity, as well as quicker healing and increased reduction of scarring.

SUMMARY OF THE INVENTION

The present invention provides a process for the therapeutic treatment and prophylaxis of wounds, burns, and other dermal disorders comprising applying an aqueous solution of from about 0.002% to about 0.5% by weight of a metal chlorite.

It is a general object of the present invention to provide compositions and methods which contribute to quicker healing of wounds, chronic non-healing wounds and other dermal disorders.

A further object of the present invention is to provide compositions and methods which aid in the reduction or elimination of scar formation.

Another object of the present invention is to provide antiseptic compositions and methods which exhibit anticollagenous activity such that the characteristics of the healed skin, such as elasticity and tensile strength, are similar to undamaged skin.

Yet another object of the present invention is to provide broad spectrum antimicrobial compositions and methods for the antiseptic treatment of dermal disorders.

Still another object of the present invention is to provide antiseptic compositions which are stable for long periods of time and can be used directly in most applications without additional preparation, mixing or activation.

Other objects, features and advantages of the present invention will become clear from the following description when read in conjunction with the drawings and appended claims.

DETAILED DESCRIPTION

As noted above, the present invention is directed to compositions and methods for facilitating the healing of dermal disorders in human skin. The composition generally comprises an aqueous solution containing a suitable amount of a metal chlorite, such as sodium chlorite. The compositions described herein are useful as wound healing agents for the therapeutic treatment of dermal wounds, trauma, burns, dermal infection, non-healing chronic wounds, decubitus ulcers, and the prophylactic prevention of decubitus wounds.

The present invention contrasts from the prior art approaches in several significant aspects. While the prior art approaches concentrate primarily on the use of compounds which are relatively strong oxidizing agents, such as chlorine dioxide, stabilized chlorine dioxide and peroxy compounds, to act essentially as an antiseptic having strong germicidal qualities, the present invention concentrates on the use of much milder oxidizing agents to facilitate the healing process. Although the mechanism by which the present invention facilitates the healing process is presently unknown, it is believed that the use of a milder oxidizing agent is less injurious to human tissue. The skin heals faster and with reduced scarring and improved skin characteristics, such as tensile strength and elasticity.

In contrast to the prior art approach of using acid induced generation of chlorine dioxide, the present invention does not employ the use of chemicals designed to liberate chlorine dioxide in solution. Rather, the present invention uses metal chlorites in such a manner as to suppress the production of chlorine dioxide. The applications of the present invention display anticollagenous activity which allows the skin to heal in a more desirable manner.

Although the compositions and methods of the present invention display antiseptic characteristics, the present invention uses a milder oxidizing agent than the prior art approaches. In this manner, the applications of the present invention act more as a slow acting germicide and as a germistat when compared to the prior art approaches. By merely functioning in the manner, the present invention allows the body's own defenses to help kill any germs (viruses, yeasts, bacteria, fungi, i.e., all types of microorganisms), resulting in a much milder action in the afflicted area.

The present invention avoids the dangers that are associated with the use of antibiotic compounds. Pathogenic microorganisms do not develop resistance to the oxidative mode of antimicrobial activity. The very low toxicity of the invention also precludes direct toxic effects on the body. This is particularly important, for example, in burn patients where the toxins from the burn wound can stress patient liver functions. The mild oxidative action of the invention does not place additional stress on the liver.

Unless otherwise specified, all parts or percentages in the specification as well as the examples are weight percentages. As used in the specification, "metal chlorites" shall refer to water soluble alkali metal chlorites and alkaline earth metal chlorites. Sodium chlorite and potassium chlorite are preferred. Sodium chlorite is particularly preferred.

In one aspect, the present invention provides a composition for therapeutic and prophylactic treatment of human skin which comprises an aqueous solution of a metal chlorite, such as sodium chlorite or potassium chlorite, in a concentration of from about 0.002% (20 ppm) to about 0.5% (5,000 ppm). The pH of the solution should be in the range of about 6.0 to about 10.0 and any stable buffer useful in the stated pH range may be used.

In a preferred embodiment of this aspect of the present invention, there is provided a composition for therapeutic and prophylactic treatment of human skin which comprises an aqueous solution of a metal chlorite, such as sodium or potassium chlorite, in a concentration of from about 0.005% (50 ppm) to about 0.2% (2,000 ppm). The pH of the solution should be in the range of from about 6.0 to about 9.0. Carbonate, borate, phosphate or combinations thereof may be used as a buffer for the solution.

In a particularly preferred embodiment, the present invention provides an antiseptic composition for the treatment and prevention of dermal disorders which comprises an aqueous solution of a metal chlorite, such as sodium or potassium chlorite, in a concentration of from about 0.02% (200 ppm) to about 0.12% (1,200 ppm). The pH of the solution should be in the range of from about 6.0 to about 9.0 and a carbonate or borate buffer is preferred. The ideal composition for each application is dependent upon the usage and nature of treatment being administered, but would fall within the range of the presently described embodiment.

In alternative embodiments, the compositions of the present invention include aqueous mixtures of metal chlorites, such as sodium or potassium chlorite, and metal chlorates, such as sodium or potassium chlorate. The total concentration of chlorites and chlorates is from about 0.002% (20 ppm) to about 0.5% (5,000 ppm) and preferably from about 0.02% (200 ppm) to about 0.12% (1,200 ppm). The pH of the solution should be in the range of from about 6.0 to about 9.0 and a carbonate or borate buffer is preferred. The ratio of chlorite to chlorate in the solution can be from about 100:0% up to about 60:40%, with the ideal composition for each application dependent upon the usage and nature of treatment being administered.

For use on human or animal skin, these compositions may be typically applied in conjunction with a gel application medium because of the ability of the gel to adhere to the skin. Any gelling agent or thickener which is non-toxic and nonreactive with the metal chlorite may be used. Cellulose gels, particularly methyl, hydroxymethyl and hydroxyethyl cellulose gels, polyvinylsulfonic acid, polyamide and silica-base gels are preferred.

The compositions of the present invention may be applied to the skin in any manner known to those skilled in this art.

The compositions may be sprayed, coated, swabbed or applied to the skin in any other manner depending upon the nature of the disorder and the location of the area of skin to be treated. The composition is allowed to remain on the affected area for a sufficient period of treatment. The composition may be reapplied to maintain an effective level of the composition throughout the period of treatment. In most cases, the composition should be applied liberally to the site, preferably as soon as possible after the infection, disease, inflammation, etc. appears. When used, gel should also be liberally applied. If the gel is absorbed or accidentally removed, it may be reapplied as necessary.

The antiseptic composition of the present invention can also be incorporated into a variety of material to produce wound dressings, compresses, and covers with antimicrobial activity for direct topical application to the dermal surface. Such wound dressings are useful for the treatment and prophylaxis of skin disease and other disorders such as those described below. Examples of material used for wound dressings which are suitable for incorporation of the inventive composition include, but are not limited to: water-permeable, flexible, porous, sponge-type material; collagen sheets; hydrophilic polymer materials with a water content of from about 10 percent to about 90 percent; open cell foam type materials of natural and artificial rubber and urethane foams; and woven or non-woven fabrics of natural or synthetic materials. The topical dressings thus treated are topically applied as needed for control of microbial infection, to speed healing, and reduce skin damage. The compositions of the present invention may also be used in soap products, toothpastes, mouthwashes, and the like.

The following are specific examples of preferred composition for specific applications of the process of the present invention.

EXAMPLE I

This example illustrates the use of the present invention for the topical treatment of fresh dermal wounds, burns, and trauma.

An aqueous solution of about 0.1% (1,000 ppm) sodium chlorite is prepared having a pH of from about 7.0 to about 8.5 using a carbonate buffer. The solution is applied directly to burned, traumatized, wounded or damaged skin by one or more of a variety of methods including, without limitation, bathing, rinsing, sponging, immersion, spraying or misting. The composition is applied to the treated area two to three times per twenty-four hour period. The antimicrobial activity of the solution when used in this manner results in pain reduction, infection control, wound closure, more rapid healing, reduced scarification with the physical and mechanical properties of the healed skin, such as elasticity and tensile strength, being nearly identical to that of the patent's undamaged skin.

EXAMPLE II

This example illustrates the use of the present invention for treatment of chronic non-healing wounds such as decubitus wounds, skin ulcers, pressure wounds and the like.

The composition prepared according to Example I is applied to the afflicted area of the skin in an appropriate manner such as bathing, sponging, spraying or misting. The treatment is applied two to three times per twenty-four hour period. This therapeutic treatment results in rapid closure and healing of chronic wounds. Additionally, scarification would be reduced and the mechanical and physical integrity of the damaged skin would be regained.

EXAMPLE III

This example illustrates the use of the present invention for treatment for cleaning, debridement, and antisepsis of dermal wounds, burns, trauma and other diseases and disorders.

The composition prepared according to Example I is applied to clean and debride afflicted dermal areas by rinse, wash, soak, immersion, spray, mist, lavage, bathing or other suitable means. The treatment is applied two to three times per twenty-four hour period. This treatment results in a cleaning of the area, removal of foreign material and debris, and control of infectious microorganisms. The resulting benefits which accrue from this usage include infection control, cleaning of tissue, and rapid wound healing.

EXAMPLE IV

This example illustrates the use of the present invention for the prophylactic treatment of dermal pressure wounds, decubitus, skin ulcers and other dermal disorder such as those often encountered by elderly people with limited mobility and, especially, bedridden patients.

An aqueous solution of from about 0.02% (200 ppm) to about 0.05% (500 ppm) sodium chlorite is prepared having a pH of from about 7.0 to about 8.5 using a carbonate buffer. The composition is administered for the prophylaxis of dermal pressure wounds, decubitus, and skin ulcers by way of hydrotherapy immersion baths. The solution, applied in this manner, prevents the formation of the described dermal wounds. The same solution may be applied by way of sponge baths, showers, spraying, misting or immersion with similar anticipated results. Treatment should be applied two to three times per twenty-four hour period.

EXAMPLE V

This example illustrates the use of the present invention for treatment of fungal skin infections known as dermatophytoses. *Tinea pedis* (Athlete's Foot), *Tinea corporis* (Ringworm), *Tinea cruris* (Jock Itch), and *Tinea capitis* are all superficial dermal mycoses which can be successfully treated by the inventive composition.

The composition prepared according to Example I is applied to the infected area of the skin in an appropriate manner by bathing, sponging, immersion, spraying or by other means. This treatment elicits the desired result of eliminating the fungal infection and returning the skin to a state of normal health. Itching, burning, and other discomfort are reduced during the course of the treatment regimen. Application as described is made one to three times per day until all evidence of the fungal infection is eliminated.

EXAMPLE VI

This example illustrates the use of the present invention for treatment of established bacterial and viral infections of the skin including, without limitation, older wounds with established bacterial infections, impetigo, acne, chancres, boils lesions, vesicular eruptions, carbuncles, pustulant sores, weeping wounds, and the like.

The composition prepared according to Example I is applied to the afflicted are in any number of ways, including, without limitation, bathing, rinsing, sponging, immersion, spraying, misting, soaking, lavage or other suitable means. Treatments are applied one to three times per day as symptoms warrant until the infection clears.

It will be clear that the present invention is well adapted to carry out the objects and attain the advantages mentioned as well as those inherent therein. While presently preferred embodiments of the invention have been described for purposes of this disclosure, numerous changes can be made which will readily suggest themselves to those skilled in the art and which are encompassed within the spirit of the invention disclosed and as defined in the appended claims.

What is claimed is:

1. A process for the therapeutic treatment and prophylaxis of wounds, burns, and dermal disorders comprising applying to a wound, burn and/or dermal disorder an aqueous solution consisting essentially of from about 0.002% to about 0.5% by weight of a metal chlorite selected from the group consisting of alkali metal chlorites and alkaline earth metal chlorites.

2. The process of claim 1 wherein the metal chlorite is sodium chlorite.

3. The process of claim 1 wherein the metal chlorite is potassium chlorite.

4. The process of claim 1 wherein the pH of the solution is in the range of from about 6.0 to about 10.0.

5. The process of claim 4 further comprising a stable buffer.

6. The process of claim 1 wherein the pH of the solution is in the range of from about 7.0 to about 7.6.

7. The process of claim 6 wherein the metal chlorite is sodium chlorite.

8. A process for the therapeutic treatment and prophylaxis of wounds, burns, and dermal disorders comprising applying to a wound, burn and/or dermal disorder an aqueous antiseptic solution consisting essentially of from about 0.002% to about 0.5% by weight of a metal chlorite selected from the group consisting of alkali metal chlorites and alkaline earth metal chlorites, wherein the wound, burn and/or dermal disorder is healed more quickly and results in healed skin having skin characteristics similar to that of undamaged skin and results in little or no scar formation.

* * * * *